United States Patent
Sargsyan et al.

(10) Patent No.: US 12,290,584 B2
(45) Date of Patent: May 6, 2025

(54) HAIR DYEING METHOD USING NATURAL DYES AND METAL SALT

(71) Applicant: Henkel AG & Co. KGaA, Duesseldorf (DE)

(72) Inventors: Lusine Sargsyan, Hamburg (DE); Hartmut Manneck, Barnitz (DE); Thomas Hippe, Appen (DE); Volkmar Vill, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 47 days.

(21) Appl. No.: 18/254,355

(22) PCT Filed: Oct. 5, 2021

(86) PCT No.: PCT/EP2021/077389
§ 371 (c)(1),
(2) Date: May 24, 2023

(87) PCT Pub. No.: WO2022/111890
PCT Pub. Date: Jun. 2, 2022

(65) Prior Publication Data
US 2024/0016714 A1    Jan. 18, 2024

(30) Foreign Application Priority Data
Nov. 25, 2020   (DE) .......................... 102020214790.6

(51) Int. Cl.
| | | |
|---|---|---|
| *A61Q 5/10* | (2006.01) | |
| *A61K 8/19* | (2006.01) | |
| *A61K 8/34* | (2006.01) | |
| *A61K 8/362* | (2006.01) | |
| *A61K 8/9789* | (2017.01) | |
| *A61Q 5/06* | (2006.01) | |

(52) U.S. Cl.
CPC .................. *A61K 8/19* (2013.01); *A61K 8/34* (2013.01); *A61K 8/362* (2013.01); *A61K 8/9789* (2017.08); *A61Q 5/065* (2013.01)

(58) Field of Classification Search
CPC . A61K 8/19; A61K 8/34; A61K 8/362; A61K 8/9789; A61K 8/347; A61Q 5/065; A61Q 5/10
USPC ............................................................ 8/424
See application file for complete search history.

(56) References Cited

U.S. PATENT DOCUMENTS

| | | | | |
|---|---|---|---|---|
| 4,946,472 A | * | 8/1990 | Motono ................... | A61Q 5/10 8/405 |
| 2012/0138079 A1 | * | 6/2012 | Knight ..................... | A61Q 5/10 132/208 |

FOREIGN PATENT DOCUMENTS

| | | | |
|---|---|---|---|
| EP | 0327345 A2 | 8/1989 | |
| WO | 2010094207 A1 | 8/2010 | |
| WO | 2010135237 A1 | 11/2010 | |
| WO | WO 2011020833 A1 * | 2/2011 | ............... A61Q 5/10 |
| WO | 2013131756 A2 | 9/2013 | |

OTHER PUBLICATIONS

Debasish Das et al. "Dyeing of Wool and Silk with Tea," vol. 4. Jan. 1, 2005 (Jan. 1, 2005). pp. 17-25, Retrieved from the Internet: http://repository.up.ac.za/bitstream/handle/2263/8449/Das_2005.pdf?sequence=1&isAllowed=y, XP055382334.

Sargsyan Lusine et al. "Tannin-Mordant Coloration with Matcha (camelia sinensis) and Iron(II)-Lactate on Human Hair Tresses," Molecules, vol. 26, No. 4, Feb. 5, 2021 (Feb. 5, 2021), p. 829, Retrieved from the Internet: https://www.ncbi.nlm.nih.gov/pmc/articles/PMC7914801/pdf/molecules-26-00829.pdfDOI:10.3390/molecules26040829, XP055877508.

* cited by examiner

*Primary Examiner* — Eisa B Elhilo
(74) *Attorney, Agent, or Firm* — Lorenz & Kopf, LLP

(57) ABSTRACT

The present disclosure relates to a process and a kit for dyeing keratin-containing fibers, in particular human hair, using selected natural dyes and an iron(II) salt. The kit includes an aqueous composition (M) and an aqueous composition (T), where the aqueous composition (M) includes a polyphenol and a buffer system. The aqueous composition (T) includes a salt of the divalent iron cation Fe(II), and optionally includes a buffer.

20 Claims, No Drawings

HAIR DYEING METHOD USING NATURAL DYES AND METAL SALT

CROSS REFERENCE TO RELATED APPLICATIONS

This application is a U.S. National-Stage entry under 35 U.S.C. § 371 based on International Application No. PCT/EP2021/077389, filed Oct. 5, 2021, which was published under PCT Article 21(2) and which claims priority to German Application No. 10 2020 214 790.6, filed Nov. 25, 2020, which are all hereby incorporated in their entirety by reference.

TECHNICAL FIELD

The present disclosure relates to a process and a kit for dyeing keratin-containing fibers, in particular human hair, using selected natural dyes and an iron(II) salt.

BACKGROUND

The desire to change one's hair color is a great need for many consumers. To satisfy this need, the cosmetic industry provides a diverse range of products. Hair dyes that achieve a particularly long-lasting coloration with high opacity are mostly oxidation dyes. These use oxidizing and alkalizing agents that can damage the hair structure. Certain cationic direct dyes are also capable of providing hair color changes with excellent fastness properties. The mentioned colorants contain synthetic dyes.

Among a growing number of consumers, there is a desire for hair dyes and hair dyeing processes based on natural dyes, even though these agents and processes are inferior to the aforementioned agents and processes in terms of fastness properties, opacity and color variety.

In addition to dyeing with henna, which is obtained from the plant *Lawsonia inermis*, coloring hair with certain polyphenols, especially tannins and pseudotannins, has been known for a long time. Such polyphenols are extracted from certain parts of plants. However, it is also possible to use powdered plant parts with high polyphenol content in the colorant. In addition, it is possible to use pure polyphenols, in particular tannic acid, according to the present disclosure. The adhesion of the polyphenol dye to the hair or keratin fibers and thus the fastness of the coloration, as well as the shade and color intensity achieved, can be positively influenced by certain divalent or trivalent metal salts.

STATE OF THE ART

Disclosure EP327345A2 discloses a composition for darkening hair, comprising a first component made up as a shampoo and containing at least one ferrous salt (i.e., a mordant), and a second component containing at least one organic compound, e.g., propyl gallate, as a coloring agent. After the application of the second component, the hair becomes dark colored as a result of the formation of a dark colored complex of iron(II) and propyl gallate. Disclosure WO2010094207A1 discloses a method of coloring hair in which the hair is first treated with a keratin reducing agent, thereby breaking up the hair structure, then a composition containing an iron (II) salt as a mordant and an antioxidant, and then a hair coloring composition containing an emollient and a polyphenol coloring agent are applied to the hair.

BRIEF SUMMARY

Methods and kits for dyeing keratin fibers are provided. A method of dyeing keratin fibers includes applying an aqueous composition (T) to the keratin fibers, where the aqueous composition (T) has a pH of from about 4.6 to about 5.6. The aqueous composition (T) includes a polyphenol, where the polyphenol is available in the Shikimate biosynthesis pathway, has at least 2 hydroxy groups, and has a molecular weight of from about 170 to about 20,000 grams per mole. The aqueous composition (T) also has a buffer system that is selected from a mixture of a moderately strong or weak acid with its conjugated or corresponding base (or the respective salt), and a mixture of a moderately strong or weak base and its conjugated or corresponding acid. The aqueous composition (T) is allowed to act on the keratin fibers for a time period of from about 30 seconds to 60 minutes, and then is rinsed from the keratin fibers. The keratin fibers may then optionally be dried. Directly thereafter, an aqueous composition (M) is applied to the keratin fibers, where the aqueous composition (M) has a pH of from about 2.5 to about 6.4. The aqueous composition (M) includes a salt of a divalent iron cation Fe(II) in an amount of from about 0.001 to about 3.0 weight percent. The aqueous composition (M) optional also includes a buffer system that is selected from a mixture of a moderately strong or weak acid with its conjugated or corresponding base (or the respective salt), and a mixture of a moderately strong or weak base and its conjugated or corresponding acid. The aqueous composition (M) is allowed to act on the keratin fibers for from about 30 seconds to about 60 minutes, and then is rinsed from the keratin fibers. The keratin fibers are then optionally dried. No elemental iron, sponge iron, copper salts, or aluminum salts are used in the method. Also, the keratin fibers have not been treated with an oxidizing agent or a reducing agent for a period of about 7 days prior to the application of the aqueous composition (T).

A kit for dyeing keratin fibers is provided in another embodiment. The kit includes an aqueous composition (T) and an aqueous composition (M). The aqueous composition (T) has a pH of from about 4.6 to about 5.6. The aqueous composition (T) includes a polyphenol, where the polyphenol is available in the Shikimate biosynthesis pathway, has at least 2 hydroxy groups, and has a molecular weight of from about 170 to about 20,000 grams per mole. The aqueous composition (T) also has a buffer system that is selected from a mixture of a moderately strong or weak acid with its conjugated or corresponding base (or the respective salt), and a mixture of a moderately strong or weak base and its conjugated or corresponding acid. The aqueous composition (M) has a pH of from about 2.5 to about 6.4. The aqueous composition (M) includes a salt of a divalent iron cation Fe(II) in an amount of from about 0.001 to about 3.0 weight percent. The aqueous composition (M) optional also includes a buffer system that is selected from a mixture of a moderately strong or weak acid with its conjugated or corresponding base (or the respective salt), and a mixture of a moderately strong or weak base and its conjugated or corresponding acid. The aqueous composition (T) is free of elemental iron, sponge iron, copper salts, and aluminum salts. The aqueous composition (M) is free of elemental iron, sponge iron, copper salts, and aluminum salts.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Task

The present disclosure was based on the task of providing a process for dyeing keratin-containing fibers, in particular human hair, which achieves a dyeing with good fastness properties, in particular with a high wash fastness.

The present disclosure was further based on the task of providing a process for dyeing keratin-containing fibers, in particular human hair, using natural dyes, which causes as little damage as possible to the keratin structure.

Another task was to provide a process for dyeing keratin-containing fibers, in particular human hair, using natural dyes, which achieves dyeing with high color intensity.

A further task was to provide a process for dyeing keratin-containing fibers, in particular human hair, using natural dyes, which achieves particularly chromatic dyeing.

Surprisingly, it was found that the dyeing process described in the patent claims achieves intense colorations with high wash fastness comparable to semi-permanent hair dyeing, i.e. oxidative hair dyeing under mild conditions (weak alkaline medium, low hydrogen peroxide concentration), but without damaging the hair structure.

An object of the present disclosure is a process for the non-oxidative dyeing of keratinous fibers, in particular human hair, with natural dyes, comprising the following process steps in the order indicated:

a) Application to the keratin fibers of an aqueous composition (T) having a pH in the range from about 4.6 to about 5.6, preferably in the range from about 4.8 to about 5.2, extremely preferably in the range from about 4.9 to about 5.0, each measured at 20° C., said composition (T) comprising:
  i. at least one polyphenol which
    is available on the Shikimate biosynthesis pathway and
    has at least 2 hydroxy groups in the molecule and
    has a molecular weight in the range from about 170 to about 20,000 g/mol; furthermore
  ii. a buffer system selected from a mixture of a moderately strong or weak acid with its conjugated or corresponding base tor the respective salt) and a mixture of a moderately strong or weak base with its conjugated or corresponding acid,
b) Allow to act for a time of about 30 seconds to about 60 minutes, preferably about 5 to about 45 minutes, most preferably about 15 to about 30 minutes,
c) Rinse the keratin fibers with water,
d) optional drying of the keratin fibers,
e) directly thereafter applying to the keratin fibers an aqueous composition (M) having a pH in the range from about 2.5 to about 6.4, preferably in the range from about 5.2 to about 6.0, particularly preferably in the range from about 5.4 to about 5.8, in each case at 20° C., said composition (M) comprising:
  iii. at least one salt of the divalent iron cation Fe(II) in an amount of about 0.001 to about 3.0 wt. %, preferably about 0.01 to about 2 wt. %, particularly preferably about 0.1 to about 1 wt. %, exceptionally preferably about 0.2 to about 0.5 wt. %, in each case based on the weight of the composition (M),
  iv. optionally a buffer system selected from a mixture of a moderately strong or weak acid with its conjugated or corresponding base (or the respective salt) and a mixture of a moderately strong or weak base with its conjugated or corresponding acid,
f) Allow to act for a time of about 30 seconds to about 60 minutes, preferably about 5 to about minutes, most preferably about 15 to about 30 minutes,
g) Rinse the keratin fibers with water,
h) optional drying of the keratin fibers, whereby no elemental iron, sponge iron, copper salts or aluminum salts are used in the process, exemplified in that the keratinous fibers have not been treated with an oxidizing agent and have not been treated with a keratin reducing agent for a period of up to about 7 days prior to the application of the composition (T).

In order to preserve the hair-protecting potential of the natural dyes, the claimed process is limited to those processes in which the keratinous fibers have not been treated with an oxidizing agent and not with a keratin-reducing agent for a period of up to about 7 days prior to the application of composition (T).

Oxidizing agents which are normally used in hair cosmetics but which are not intended for hair treatment according to the present disclosure, even as pretreatment, include hydrogen peroxide, persulfates, perbromates, percarbonates, perborates and percarbamides. In the context of the present disclosure, atmospheric oxygen does not constitute an oxidizing agent.

The keratin-reducing compounds which are normally used in hair cosmetics but which are not intended to be used for hair treatment according to the present disclosure, even as pretreatment, include thioglycolic acid, thiolactic acid, cysteine, N-acetylcysteine, cysteamine and the salts of the above compounds, furthermore sulfites, in particular sodium sulfite, hydrogen sulfites, in particular sodium hydrogen sulfite, and metabisulfites, in particular sodium metabisulfite, as well as mixtures of these keratin-reducing compounds.

As a first step in the process, an aqueous composition (T) is applied to the hair to be colored, which is preferably dry, which, with the aid of a buffer system, is selected from a mixture of a moderately strong or weak acid with its conjugate or corresponding base (or des respective salt) and a mixture of a moderately strong or weak base with its conjugate or corresponding acid, to a pH in the range from about 4.6 to about 5.6, preferably in the range from about 4.8 to about 5.2, is extremely preferred in the range from about 4.9 to about 5.0, each measured at 20° C., and which contains at least one polyphenol as a natural dye which—according to Quideau's definition of polyphenols—is obtainable via the shikimate biosynthetic pathway and also at least 2 Has hydroxyl groups in the molecule and whose molar mass is in the range from about 170 to about 20,000 g/mol, preferably about 290 to about 3000 g/mol. Polyphenols preferred according to the present disclosure have at least about 12 hydroxy groups and at least five phenyl groups.

Preferred dyeing processes according to the present disclosure are exemplified in that the at least one polyphenol i. is selected from tannins and pseudotannins and mixtures thereof.

Tannins are phytochemical products of secondary metabolism, more specifically, the shikimate biosynthetic pathway, in plants. They can be obtained from various parts of plants, preferably from the wood, especially the stem wood, furthermore from barks, leaves, seeds, fruits, galls, pods, pods or roots.

Preferred tannins used according to the present disclosure are selected from hydrolysable tannins and condensed tannins.

The hydrolysable tannins have the molecule gallic acid as their basic building block. Gallic acid (170.12 g/mol) itself is not called tannin, but pseudotannin.

The hydrolysable tannins can be divided into gallotannins and ellagitannins. Gallotannin is also known as tannic acid.

The condensed tannins have flavan-3-ols as their basic building block. Flavan-3-ols (226.27 g/mol) themselves are not called tannins, but pseudotannins. Preferred condensed tannins used include proanthocyanidins, procyanidins, flavonoids, propelargonidins, prodelphinides, prosetinidins, proteracacinidins, proguibourtinidins, and prorobinetidins. Among the flavonoids, the catechins are particularly preferred according to the present disclosure. Pseudotannins preferred according to the present disclosure are gallic acid, flavan-3-ols and chlorogenic acid.

Dyeing processes preferred according to the present disclosure are exemplified in that the at least one polyphenol i., preferably selected from tannins and pseudotannins, is obtained from at least one plant selected from *Camellia sinensis*, *Acacia* spp., in particular *Acacia mollissima*, *Acacia negra* and *Acacia dealbata*, *Olea europaea* (olive tree), *Schinopsis lorentzii*, *Aspidosperma quebracho-blanco*, *Rubiaceae Coffea arabica* L., *Rheum* spp., in particular *Rheum palmatum*, *Pinus* spp., *Picea* spp, *Vitis vinifera*, *Lawsonia inermis* (red henna), *Quercus* spp. (oak), especially *Quercus macrolepis*, *Curcuma longa*, *Juglans* spp, especially *Jugians nigra* and *Juglans regia*, the tara tree (*Tara spinosa*, *Caesalpinia spinosa*, *Caesalpinia tinctoria*), chestnut (*Castanea sativa*), tanbark (*Rhus coriaria*), the wig tree (*Rhus cotinus*, *Cotinus coggygria*), *Haematoxylum brasiletto* L. (Brazilian bloodwood tree), *Haematoxylum campecilianum* (bloodwood tree, bluewood tree, campeche tree), and *Maclura tinctoria* (dyer's mulberry tree), and mixtures thereof.

Further dyeing processes preferred according to the present disclosure are exemplified in that the at least one polyphenol i., which is preferably selected from tannins and pseudotannins, is present in the form of at least one ground plant part. Plant parts preferred according to the present disclosure, which can be used preferably in ground form according to the present disclosure, are leaves, fruit husks, seed coats, rhizome (rootstock) and roots.

Further dyeing methods preferred according to the present disclosure are exemplified in that the at least one polyphenol i., which is preferably selected from tannins and pseudotannins, is in the form of at least one plant part extract. Plant parts preferred according to the present disclosure, from which extracts preferred according to the present disclosure can be obtained, are the stem wood, the heartwood, furthermore barks, leaves, seeds, fruits, galls, pods, pods and roots. Suitable extraction agents are water, in particular hot water at a temperature of 45-100° C., furthermore $C_1$-$C_4$ alkanols and $C_2$-$C_4$ polyols, in particular ethanol, isopropanol, n-propanol, ethylene glycol, 1,2-propanediol, glycerol and 1,3-butylene glycol, as well as mixtures of these extraction agents, in particular mixtures of water and at least one $C_1$-$C_4$ alkanol, mixtures of water and at least one C2-C4 polyol, particularly preferably water/ethanol mixtures.

Particularly preferred dyeing processes according to the present disclosure are exemplified in that the at least one polyphenol i., which is preferably selected from tannins and pseudotannins, is used in the form of matcha, i.e. the powder from dried leaves of *Camellia sinensis*. In this connection, exceptionally preferred dyeing processes according to the present disclosure are exemplified in that the aqueous composition (T) contains, in each case based on its weight, matcha in an amount of about 0.3 to about 50 wt. %, preferably about 1 to about 20 wt. %, particularly preferably about 3 to about 15 wt. %, exceptionally preferably about 8 to about 10 wt. %.

Further coloring processes particularly preferred according to the present disclosure are exemplified in that the at least one polyphenol i., preferably selected from tannins and pseudotannins, is used in the form of an extract from the bark of *Acacia dealbata*, the bark of *Acacia negra* or the bark of *Acacia mollissima*, the extract having been obtained by extraction with water, preferably with water of a temperature of about 45 to about 100° C. The extract itself is preferably used in powder form, obtainable by drying, preferably spray drying, the aqueous extract.

Further dyeing processes particularly preferred according to the present disclosure are exemplified in that the at least one polyphenol i., which is preferably selected from tannins and pseudotannins, is used in the form of an extract from the bark of *Pinus* spp. (pine), the extract having been obtained by extraction with water, preferably with water having a temperature of about 45 to about 100° C. The extract itself is preferably used in powder form, obtainable by drying, preferably spray drying, the aqueous extract.

Further dyeing processes particularly preferred according to the present disclosure are exemplified in that the at least one polyphenol i., which is preferably selected from tannins and pseudotannins, is used in the form of an extract from the bark of *Picea* spp. (spruce), the extract having been obtained by extraction with water, preferably with water of a temperature of about 45 to about 100° C. The extract itself is preferably used in powder form, obtainable by drying, preferably spray drying, the aqueous extract.

Further dyeing processes particularly preferred according to the present disclosure are exemplified in that the at least one polyphenol i., preferably selected from tannins and pseudotannins, is used in the form of an extract from the leaves of the olive tree (*Olea europea*), the extract having been obtained by extraction with water, preferably with water of a temperature of about 45 to about 100° C. The extract itself is preferably used in concentrated form, obtainable by partial distillation of the extractant after extraction, as a viscous liquid. Other extracts of olive leaves preferred according to the present disclosure are used in powder form, obtainable by drying, preferably spray drying, the aqueous extract.

Further dyeing processes particularly preferred according to the present disclosure are exemplified in that the at least one polyphenol i., preferably selected from tannins and pseudotannins, is used in the form of an extract from the stem wood of *Schinopsis lorentzii* (red quebracho), the extract having been obtained by extraction with water, preferably with water of a temperature of about 45 to about 100° C. The extract itself is preferably used in concentrated form, obtainable by partial distillation of the extractant after extraction, as a viscous liquid. Other extracts from the stem wood of *Schinopsis lorentzii* preferred according to the present disclosure are used in powder form, obtainable by drying, preferably spray drying, the aqueous extract.

Further dyeing processes particularly preferred according to the present disclosure are exemplified in that the at least one polyphenol i., preferably selected from tannins and pseudotannins, is used in the form of an extract from the stem wood of *Aspidosperma quebracho-blanco* (white *quebracho*), the extract having been obtained by extraction with water, preferably with water of a temperature of about 45 to about 100° C. The extract itself is preferably used in concentrated form, obtainable by partial distillation of the extractant after extraction, as a viscous liquid. Other extracts from the stem wood of *Aspidosperma quebracho-blanco* preferred according to the present disclosure are used in powder form, obtainable by drying, preferably spray drying, the aqueous extract.

Further dyeing processes particularly preferred according to the present disclosure are exemplified in that the at least one polyphenol i., preferably selected from tannins and pseudotannins, is used in the form of an extract from the seeds of *Rubiaceae Coffea arabica* L. (coffee plant), the extract having been obtained by extraction with a water/ethanol mixture. The extract itself is preferably used in powder form, obtainable by drying, preferably spray drying, the aqueous extract. Other extracts from the seeds of *Rubiaceae Coffea arabica* L. preferred according to the present disclosure are preferably used in concentrated form, obtainable by partial distillation of the extractant after extraction, as a viscous liquid.

Further dyeing methods particularly preferred according to the present disclosure are exemplified in that the at least one polyphenol i., preferably selected from tannins and pseudotannins, is obtained in the form of an extract from the rhizomes (rhizome) of *Rheum* spp., in particular *Rheum palmatum*, further preferably *Rheum palmatum* var. *Tanguticum*, the extract having been obtained by extraction with water or with a water/ethanol mixture.

Further coloring processes particularly preferred according to the present disclosure are exemplified in that the at least one polyphenol i., preferably selected from tannins and pseudotannins, is used in the form of an extract from the seeds of *Vitis vinifera* (grapes), the extract having been obtained by extraction with water or with a water/ethanol mixture.

Further dyeing processes particularly preferred according to the present disclosure are exemplified in that the at least one polyphenol i., which is preferably selected from tannins and pseudotannins, is used in the form of red henna powder, i.e. the powder from dried leaves of *Lawsonia inermis*.

Further coloring processes particularly preferred according to the present disclosure are exemplified in that the at least one polyphenol i., which is preferably selected from tannins and pseudotannins, is used in the form of an extract from the fruits and/or the fruit cups of *Quercus* spp., the extract having been obtained by extraction with water, preferably with water of a temperature of about 45 to about 100° C. The extract itself is preferably used in powder form, obtainable by drying, preferably spray drying, the aqueous extract. According to the present disclosure, the use of Valonea, the extract from the fruit cups and/or fruits of *Quercus macrolepis*, is particularly preferred.

Further dyeing methods particularly preferred according to the present disclosure are exemplified in that the at least one polyphenol i., which is preferably selected from tannins and pseudotannins, is used in the form of an extract from the rhizomes (rhizomes) of *Curcuma longa*, the extract preferably having been obtained by extraction with water or with a water/ethanol mixture.

Further coloring processes particularly preferred according to the present disclosure are exemplified in that the at least one polyphenol i., which is preferably selected from tannins and pseudotannins, is used in the form of an extract from the ground fruit peels of *Juglans* spp, in particular of *Juglans nigra* and *Juglans regia*, the extract preferably having been obtained by extraction with water or with a water/ethanol mixture.

Further dyeing processes particularly preferred according to the present disclosure are exemplified in that the at least one polyphenol i., which is preferably selected from tannins and pseudotannins, is used in the form of an extract from the fruit pods of the tara tree (*Caesalpinia spinosa*), the extract having been obtained by extraction with water, preferably with water of a temperature of about 45 to about 1000° C. The extract itself is preferably used in powder form, obtainable by drying, preferably spray drying, the aqueous extract.

Further coloring processes particularly preferred according to the present disclosure are exemplified in that the at least one polyphenol i., preferably selected from tannins and pseudotannins, is used in the form of an extract from chestnut wood (*Castatzeu sativa*), the extract having been obtained by extraction with water, preferably with water of a temperature of about 45 to about 100° C. The extract itself is preferably used in powder form, obtainable by drying, preferably spray drying, the aqueous extract.

Further dyeing processes particularly preferred according to the present disclosure are exemplified in that the at least one polyphenol i., which is preferably selected from tannins and pseudotannins, is used in the form of an extract from the leaves of tanner's sumach (*Rhus coriaria*), the extract having been obtained by extraction with water, preferably with water of a temperature of about 45 to about 100° C. The extract itself is preferably used in powder form, obtainable by drying, preferably spray drying, the aqueous extract.

Further dyeing processes particularly preferred according to the present disclosure are exemplified in that the at least one polyphenol i., which is preferably selected from tannins and pseudotannins, is used in the form of an extract from the leaves of the wig tree (*Rhus cotinus, Cotinus coggygria*), the extract having been obtained by extraction with water, preferably with water of a temperature of about 45 to about 100° C. The extract itself is preferably used in powder form, obtainable by drying, preferably spray drying, the aqueous extract.

Further dyeing processes particularly preferred according to the present disclosure are exemplified in that the at least one polyphenol i., which is preferably selected from tannins and pseudotannins, is used in the form of an extract from the heartwood of the Brazilian bloodwood tree ((*Haematoxylitin brasiletto* L.), the extract having been obtained by extraction with water, preferably with water of a temperature of about 45 to about 100° C. The extract itself is preferably used in concentrated form, obtainable by partial distillation of the extractant after extraction, as a viscous liquid. Other extracts from the heartwood of *Haematoxylum brastietto* L. preferred according to the present disclosure are used in powder form, obtainable by drying, preferably spray drying, the aqueous extract.

Further dyeing processes particularly preferred according to the present disclosure are exemplified in that the at least one polyphenol i., which is preferably selected from tannins and pseudotannins, is used in the form of an extract from the heartwood of the Brazilian bloodwood tree (*Haemaioxylum campechicmm*, also known as the bluewood tree or campeche tree), the extract having been obtained by extraction with water, preferably with water of a temperature of about 45 to about 100° C. The extract itself is preferably used in concentrated form, obtainable by partial distillation of the extractant after extraction, as a viscous liquid. Other extracts from the heartwood of *Haematoxylum compechianum* preferred according to the present disclosure are used in powder form, obtainable by drying, preferably spray drying, the aqueous extract.

Further dyeing processes particularly preferred according to the present disclosure are exemplified in that the at least one polyphenol i., which is preferably selected from tannins and pseudotannins, is used in the form of an extract from the heartwood of the dyer's mulberry tree (*Machura tinctoria*, also *Chlorophora tinctoria* or *Morus tinctoria*), the extract having been obtained by extraction with water, preferably with water of a temperature of about 45 to about 100° C. The extract itself is preferably used in concentrated form, obtainable by partial distillation of the extractant after extraction, as a viscous liquid. Other extracts from the heartwood of *Haematoxylum brasiletto* L. preferred according to the present disclosure are used in powder form, obtainable by drying, preferably spray drying, the aqueous extract.

Dyeing processes preferred according to the present disclosure are exemplified in that the aqueous composition (T) contains, in each case by weight, at least one polyphenol i., which is preferably selected from tannins and pseudotannins, in an amount of about 0.1 to about 20 wt. %, preferably about 0.2 to about 15 wt. %, particularly preferably about 1 to about 10 wt. %, exceptionally preferably about 2 to about 6 wt. %.

The plant parts and plant part extracts used in dyeing processes preferred according to the present disclosure, which contain the at least one polyphenol i., which is preferably selected from tannins and pseudotannins, usually have, based on their weight, a total content of polyphenols i. of about 10 to about 100 wt. %, preferably about 15 to about 95 wt. %, particularly preferably about 20 to about 80 wt. %, exceptionally preferably about 30 to about 70 wt. %.

Extremely preferred dyeing processes according to the present disclosure are therefore exemplified in that the aqueous composition (T) contains, in each case by weight, at least one plant part or plant part extract containing at least one polyphenol i., preferably selected from tannins and pseudotannins, in an amount of about 0.5 to about 50 wt. %, preferably about 1 to about 30 wt. %, particularly preferably about 5 to about 20 wt. %, exceptionally preferably about 10 to about 15 wt. %.

The aqueous composition (T) used according to the present disclosure further comprises a buffer system selected from a mixture of a moderately strong or weak acid with its conjugate or corresponding base (or the respective salt) and a mixture of a moderately strong or weak base with its conjugate or corresponding acid.

Corresponding acid-base pairs suitable according to the present disclosure are those which stabilize the aqueous composition (T) used according to the present disclosure in the pH range from about 4.6 to about 5.6, preferably in the range from about 4.8 to about 5.2, exceptionally preferably in the range from about 4.9 to about 5.0, in each case measured at 20° C. Buffer systems particularly preferred according to the present disclosure are selected from Mixtures of citric acid and its salts, in particular the alkali metal citrates, especially the sodium salts, in particular trisodium citrate, Mixtures of tartaric acid and its salts, in particular the alkali metal tartrates, especially the potassium salts, in particular potassium hydrogen tartrate, Mixtures of phthalic acid and its salts, in particular the potassium salts, especially potassium hydrogen phthalate, Mixtures of lactic acid and its salts, especially lactic acid/sodium lactate mixtures, Mixtures of gluconic acid and its salts, especially gluconic acid/sodium gluconate mixtures, Mixtures of succinic acid and its salts, especially the sodium salts, in particular sodium hydrogen succinate and disodium succinate, as well as Mixtures of malic acid and its salts, in particular the sodium salts, especially sodium hydrogen malate and disodium malate.

A particularly preferred buffer system according to the present disclosure is formed from citric acid and at least one sodium salt of citric acid; mixtures of citric acid and trisodium citrate are exceptionally preferred.

Other buffer systems, e.g. acetic acid/sodium acetate, are also suitable in principle according to the present disclosure. However, due to the vinegar odor, such a buffer is not acceptable for the manufacture of a cosmetic market product.

Dyeing processes preferred according to the present disclosure are exemplified in that the aqueous composition (T) contains, in each case based on its weight, a buffer system in an amount of about 0.5 to about 5 wt. %, preferably about 0.8 to about 4.5 wt. %, particularly preferably about 1.5 to about 3.5 wt. %, exceptionally preferably about 2.1 to about 3.0 wt. %.

Dyeing processes preferred according to the present disclosure are exemplified in that the aqueous composition (T) contains, in each case based on its weight, as buffer system about to about 1.5 wt. %, preferably about 0.3 to about 1.4 wt. %, particularly preferably about 0.5 to about 1.1 wt. %, extremely preferably about 0.6 to about 0.9 wt. % citric acid and about 0.3 to about 3.5 wt. %, preferably about 0.5 to about 3.1 wt. %, particularly preferably about 1.0 to about 2.4 wt. %, extremely preferably about 1.5 to about 2.1 wt. % trisodium citrate.

Dyeing processes preferred according to the present disclosure are exemplified in that the aqueous composition (T) contains, in each case based on its weight, as buffer system about to about 1.5 wt. %, preferably about 0.3 to about 1.4 wt. %, particularly preferably about 0.5 to about 1.1 wt. %, extremely preferably about 0.6 to about 0.9 wt. % gluconic acid and about 0.3 to about 3.5 wt. %, preferably about 0.5 to about 3.1 wt. %, particularly preferably about 1.0 to about 2.4 wt. %, extremely preferably about 1.5 to about 2.1 wt. % sodium gluconate.

Dyeing processes preferred according to the present disclosure are exemplified in that the aqueous composition (T) contains, in each case based on its weight, as buffer system about to about 1.5 wt. %, preferably about 0.3 to about 1.4 wt. %, particularly preferably about 0.5 to about 1.1 wt. %, extremely preferably about 0.6 to about 0.9 wt. % lactic acid and about 0.3 to about 3.5 wt. %, preferably about 0.5 to about 3.1 wt. %, particularly preferably about 1.0 to about 2.4 wt. %, extremely preferably about 1.5 to about 2.1 wt. % sodium lactate.

Dyeing processes preferred according to the present disclosure are exemplified in that the aqueous composition (T) contains, in each case based on its weight, as buffer system about to about 1.5 wt. %, preferably about 0.3 to about 1.4 wt. %, particularly preferably about 0.5 to about 1.1 wt. %, extremely preferably about 0.6 to about 0.9 wt. % succinic acid and about 0.3 to about 3.5 wt. %, preferably about 0.5 to about 3.1 wt. %, particularly preferably about 1.0 to about 2.4 wt. %, extremely preferably about 1.5 to about 2.1 wt. % disodium succinate.

Dyeing processes preferred according to the present disclosure are exemplified in that the aqueous composition (T) contains, in each case based on its weight, as buffer system about to about 1.5 wt. %, preferably about 0.3 to about 1.4 wt. %, particularly preferably about 0.5 to about 1.1 wt. %, extremely preferably about 0.6 to about 0.9 wt. % succinic acid and about 0.3 to about 3.5 wt. %, preferably about 0.5 to about 3.1 wt. %, particularly preferably about 1.0 to about 2.4 wt. %, extremely preferably about 1.5 to about 2.1 wt. % sodium hydrogen succinate.

Dyeing processes preferred according to the present disclosure are exemplified in that the aqueous composition (T) contains, in each case based on its weight, as buffer system about to about 1.5 wt. %, preferably about 0.3 to about 1.4 wt. %, particularly preferably about 0.5 to about 1.1 wt. %, extremely preferably about 0.6 to about 0.9 wt. % malic acid and about 0.3 to about 3.5 wt. %, preferably about 0.5 to about 3.1 wt. %, particularly preferably about 1.0 to about 2.4 wt. %, extremely preferably about 1.5 to about 2.1 wt. % disodium malate.

Dyeing processes preferred according to the present disclosure are exemplified in that the aqueous composition (T) contains, in each case based on its weight, as buffer system about to about 1.5 wt. %, preferably about 0.3 to about 1.4 wt. %, particularly preferably about 0.5 to about 1.1 wt. %, extremely preferably about 0.6 to about 0.9 wt. % malic acid and about 0.3 to about 3.5 wt. %, preferably about 0.5 to about 3.1 wt. %, particularly preferably about 1.0 to about 2.4 wt. %, extremely preferably about 1.5 to about 2.1 wt. % sodium hydrogen malate.

In compositions (T) preferably used according to the present disclosure, the water content is about 40 to about 95 wt. %, preferably about 50 to about 90 wt. %, particularly preferably about 60 to about 85 wt. %, in each case based on the weight of the composition (T).

A further feature of the dyeing process according to the present disclosure is that, after application to the keratin fibers, the composition (T) is allowed to act there for a time of about 30 seconds to about 60 minutes, preferably about 5 to about 45 minutes, particularly preferably about 15 to about 30 minutes.

After the exposure time for the composition (T) has elapsed, the keratin fibers are rinsed with water to wash out the composition (T).

Optionally, the keratin fibers can be dried after this rinsing step. Drying can be done with an absorbent cloth, for example a towel. The towel-dried hair can optionally still be partially or completely dried with a hair dryer or other heat dispenser. It is also possible to let the keratin fibers dry in the air.

A further feature of the dyeing process according to the present disclosure is that, directly after the rinsing of the composition (T) and, if appropriate, directly after the optional drying step, an aqueous composition (M) is applied to the keratin fibers which has a pH in the range from about 2.5 to about 6.4, preferably in the range from about 5.2 to about 6.0, particularly preferably in the range from about 5.4 to about 5.8, in each case at 20° C. (process step e).

In this context, the indication "directly afterwards" means above all that no further composition is applied to the keratin fibers between the obligatory process steps c) and e). The specification "immediately afterwards" still means a period of time from about 1 second to a maximum of about 4 hours, preferably from about 1 second to about 1.5 hours.

The composition (M) used according to the present disclosure has a pH in the range from about 2.5 to about 6.4, preferably in the range from about 5.2 to about 6.0, particularly preferably in the range from about 5.4 to about 5.8, in each case at 20° C., and contains the following:
  iii. at least one salt of the divalent iron cation Fe(II) in an amount of about 0.001 to about 3.0 wt. %, preferably about 0.01 to about 2 wt. %, particularly preferably about 0.1 to about 1 wt. %, exceptionally preferably about 0.2 to about 0.5 wt. %, in each case based on the weight of the composition (M),
  iv. optionally a buffer system selected from a mixture of a moderately strong or weak acid with its conjugate or corresponding base (or the respective salt) and a mixture of a moderately strong or weak base with its conjugate or corresponding acid.

A further essential ingredient of the dyeing process according to the present disclosure is the at least one salt of the divalent iron cation Fe(II) in an amount of about 0.001 to about 3.0 wt. %, preferably about 0.01 to about 2 wt. %, particularly preferably about 0.1 to about 1 wt. %, exceptionally preferably about 0.2 to about 0.5 wt. %, in each case based on the weight of the composition (M), no copper salts and no aluminum salts being used in the entire process. The sequential application of the Fe(II) salt used according to the present disclosure improves the durability of the dye on the keratin fibers and thus the fastness, in particular the wash fastness, of the dyeing. According to the present disclosure, "divalent" means an iron salt whose cationic portion comprises iron with the oxidation state "two".

As anionic counterion for the at least one Fe(II) salt, anions which are physiologically compatible are preferred according to the present disclosure. These preferably include halides, particularly preferably chlorides, sulfates and the anions of C1-C6 carboxylic acids, exceptionally preferably lactic acid, gluconic acid, citric acid, acetic acid, propionic acid, oxalic acid, malonic acid, succinic acid, glutaric acid, galactaric acid (mucic acid), tartaric acid and malic acid, and mixtures of these anions.

Thus, dyeing processes preferred according to the present disclosure are exemplified in that the composition (M) contains as Fe(II) salt at least one compound selected from iron(II) lactate, iron(II) gluconate, iron(II) citrate, iron(II) chloride, ferrous sulfate, ferrous acetate, ferrous propionate, ferrous oxalate, ferrous malonate, ferrous succinate, ferrous glutarate, ferrous galactarate, ferrous tartrate and ferrous malate, and mixtures of these salts in an amount of about 0.001 to about 3.0 wt. %. -%, preferably about 0.01 to about 2 wt. %, particularly preferably about 0.1 to about 1 wt. %, exceptionally preferably about 0.2 to about 0.5 wt. %, in each case based on the weight of the composition (M).

If the composition (M) contains several Fe(II) salts, their total amount is about to about 3.0 wt. %, preferably about 0.01 to about 2 wt. %, particularly preferably about 0.1 to about 1 wt. %, exceptionally preferably about 0.2 to about 0.5 wt. %, in each case based on the weight of the composition (M).

Dyeing processes particularly preferred according to the present disclosure are exemplified in that the composition (M) contains iron(II) lactate as Fe(II) salt in an amount of about 0.001 to about 3.0 wt. %, preferably about 0.01 to about 2 wt. %, particularly preferably about 0.1 to about 1 wt. %, exceptionally preferably about 0.2 to about 0.5 wt. %, in each case based on the weight of the composition (M).

Optionally, the composition (M) used according to the present disclosure may contain a buffer system as described above for composition (T).

In compositions (M) preferably used according to the present disclosure, the water content is about 40 to about 98 wt. %, preferably about 50 to about 97 wt. %, particularly preferably about 60 to about 90 wt. %, in each case based on the weight of the composition (M).

Further dyeing processes particularly preferred according to the present disclosure are exemplified by the fact that no basic amino acids are used in the process. Surprisingly, it was found that the presence of basic amino acids, such as arginine, lysine, histidine or ornithine in particular, can affect the staining result.

The composition (M) used according to the present disclosure is free from polyphenols
  obtainable by the shikimate biosynthetic route, and
  having at least 2 hydroxyl groups in the molecule and have a molecular weight in the range of about 170 to about 20,000 g/mol.

The compositions (T) and compositions (M) used according to the present disclosure and preferred according to the present disclosure can optionally contain further additives to optimize the application properties of these compositions. Preferred additives are in particular thickeners that ensure that the compositions (T) and compositions (M) remain better on the hair during application.

Compositions (T) and compositions (M) particularly preferred according to the present disclosure contain at least one or more hydrophilic thickener, preferably selected from polysaccharides, which may be chemically and/or physically modified. According to the present disclosure, compounds from the group of polysaccharides are particularly preferred as hydrophilic thickeners, since the backbones of the polysaccharides are of natural origin and biodegradable. Preferred hydrophilic polysaccharide thickeners are selected from celluloses, cellulose ethers of C1-C4 alcohols, cellulose esters, xanthan gum, alginic acids (as well as their corresponding physiologically acceptable salts, the alginates), agar (with the polysaccharide agarose present in agar as the main constituent), starch fractions and starch derivatives such as amylose, amylopectin and dextrins, karaya gum, locust bean gum, gum arabic, pectins, dextrans and guar gum, and mixtures thereof.

Cellulose ethers of C1-C4 alcohols and cellulose esters preferred according to the present disclosure are selected from methyl celluloses, ethyl celluloses, hydroxyalkyl celluloses (such as hydroxyethyl cellulose), methylhydroxyalkyl celluloses and carboxymethyl celluloses (such as those with the INCI designation cellulose gum) as well as their physiologically compatible salts.

In preferred embodiments, for reliable viscosity adjustment and residue-free application to keratin fibers and the scalp, xanthan gum is included as a hydrophilic thickener. In further preferred embodiments, with regard to reliable viscosity adjustment and residue-free application to keratin fibers and the scalp, carboxymethylcellulose (preferably carboxymethylcellulose with the INCI designation cellulose gum) is included as a hydrophilic thickener. Carboxymethyl cellulose may be included as the sole hydrophilic thickener in a preferred embodiment. A combination of carboxymethyl cellulose and hydroxyethyl cellulose is particularly preferred.

A combination of carboxymethyl cellulose and xanthan (preferably xanthan with the INCI designation xanthan gum) may also be preferred according to the present disclosure.

Compositions (T) and compositions (M) particularly preferred according to the present disclosure contain independently of one another at least one hydrophilic thickener in a total amount of from about 0.1 to about 5 wt. %, preferably from about 0.5 to about 4 wt. %, further preferably from about 1 to about 3.5 wt. % and very particularly preferably from about 1.2 to about 2 wt. %, in each case based on the weight of the respective composition (T) or composition (M).

In a further preferred embodiment of the present disclosure, the compositions (T) and compositions (M) used according to the present disclosure contain, in each case based on their weight, independently of one another about 0.1 to about 3 wt. %, preferably about 0.5 to about 2.5 wt. %, more preferably about 1.2 to about 2.0 wt. %, of xanthan gum.

In another preferred embodiment of the present disclosure, the compositions (T) and compositions (M), used according to the present disclosure each independently contain, by weight, from about 0.1 to about 4 wt. %, preferably from about 1 to about 2.8 wt. %, of carboxymethyl cellulose.

In another preferred embodiment of the present disclosure, the compositions (T) and compositions (M) used in accordance with the present disclosure each independently contain, by weight, from about 0.1 to about 3 wt. %, preferably from about 0.5 to about 2.5 wt. %, more preferably from about 1.2 to about 2.0 wt. %, of hydroxyethylcellulose.

Compositions (T) and compositions (M) particularly preferred according to the present disclosure independently contain at least one organic solvent having a phenyl group in the molecule. Preferably, this solvent is selected from phenoxyethanol, benzyl alcohol, and mixtures thereof. Surprisingly, it was found that such aromatic solvents can have a positive effect on the dyeing results of the dyeing process according to the present disclosure; this was observed in particular when the composition (T) contains such an aromatic solvent.

In a further preferred embodiment of the present disclosure, the compositions (T) and compositions (M) used according to the present disclosure contain, in each case based on their weight, independently of one another about 0.1 to about 3 wt. %, preferably about 0.5 to about 2.5 wt. %, further preferably about 0.8 to about 1.0 wt. %, of at least one organic solvent having a phenyl group in the molecule. In a further preferred embodiment of the present disclosure, the compositions (T) and compositions (M) used according to the present disclosure contain, in each case based on their weight, independently of one another about 0.1 to about 3 wt. %, preferably about 0.5 to about 2.5 wt. %, further preferably about 0.8 to about 1.0 wt. %, of at least one organic solvent selected from phenoxyethanol, benzyl alcohol and mixtures thereof.

Particularly preferred dyeing processes according to the present disclosure are exemplified in that at least one of the composition (T) or composition (M) contains, independently of one another, at least one aliphatic solvent selected from $C_1$-$C_4$-alkanols and $C_2$-$C_4$-polyols, in particular selected from ethanol, isopropanol,-n-propanol, ethylene glycol, 1,2-propanediol, glycerol and 1,3-butylene glycol, and mixtures of these solvents, but only in a total amount of about 0.01 to about 8 wt. %, preferably about 0.1 to about 6 wt. %, particularly preferably about 0.5 to about 4 wt. %, in each case based on the weight of the composition (T) or composition (M).

Other dyeing processes particularly preferred according to the present disclosure are exemplified in that neither composition (T) nor composition (M) contains an aliphatic solvent selected from $C_1$-$C_4$ alkanols and $C_2$-$C_4$ polyols.

In order to make the compositions (T) and (M) used according to the present disclosure also sensory attractive for the user, further dyeing processes particularly preferred according to the present disclosure are exemplified in that at least one of the compositions (T) or compositions (M) independently contains at least one perfume oil containing at least one fragrance compound or odorant compound.

The definition of a fragrance within the meaning of the present application corresponds to the definition customarily used in the art, as it can be taken from the RÖMPP Chemie Lexikon, as of December 2007. According to this, a fragrance is a chemical compound with smell and/or taste that excites the receptors of the hair cells of the olfactory system (adequate stimulus). The physical and chemical properties required for this are a low molar mass of maximum 300 g/mol, a high vapor pressure, minimal water and high lipid solubility as well as weak polarity and the presence of at least one osmophoric group in the molecule. In order to distinguish volatile, low-molecular substances which are normally, and also for the purposes of the present application, not considered and used as perfumes but primarily as solvents, such as ethanol, propanol, isopropanol and acetone, from perfumes of the present disclosure, perfumes of the present disclosure have a molecular weight of about 74 to about 300 g/mol, contain at least one osmophoric group in the molecule and have an odor and/or taste, that is to say, they excite the receptors of the hair cells of the olfactory system. Examples of fragrance and aromatic compounds of the ester type are benzyl acetate, phenoxyethyl isobutyrate, p-tert. butylcyclohexyl acetate, linalyl acetate, dimethylbenzylcarbinyl acetate (DMBCA), phenylethyl acetate, benzyl acetate, ethylmethylphenylglycinate, allylcyclohexyl propionate, styrene allyl propionate, benzyl salicylate, cyclohexyl salicylate, floramate, melusat and jasmacyclate. Examples of fragrance and aromatic compounds of the ether type are benzyl ethyl ether and Ambroxan, examples of fragrance and aromatic compounds of the aldehyde type are the linear alkanals with 8-18 C atoms, citral, citronellal, citronellyloxy-acetaldehyde, cyclamenaldehyde, lily and bourgeonal, Examples of odoriferous compounds of the ketone type are jonones, alpha-isomethylionone and methylcedryl ketone; examples of odoriferous compounds of the alcohol type are anethole, citronellol, eugenol, geraniol, linalool, phenylethyl alcohol and terpineol; examples of odoriferous compounds of the terpene type are limonene and pinene. Examples of fragrance and scent compounds are pine, citrus, jasmine, patchouli, rose, ylang oil, muscatel sage oil, chamomile oil, clove oil, mint oil, cinnamon leaf oil, lime blossom oil, juniper berry oil, vetiver oil, olibanum oil, *galbanum* oil, labdanum oil, orange blossom oil, neroli oil, orange peel oil and sandalwood oil, furthermore the essential oils like *angelica* root oil, anise oil, *arnica* blossom oil, basil oil, bay oil, bergamot oil, champaca blossom oil, silver fir oil, silver fir cone oil, elemi oil, *eucalyptus* oil, fennel oil, spruce needle oil, geranium oil, ginger grass oil, guaiac wood oil, gurjun balsam oil, helichrysum oil, ho-oil, ginger oil, Iris oil, cajeput oil, calamus oil, chamomile oil, camphor oil, canaga oil, cardamom oil, *cassia* oil, pine needle oil, copaïva balsam oil, coriander oil, spearmint oil, caraway oil, cumin oil, lavender oil, lemongrass oil, lime oil, tangerine oil, lemon balm oil, musk seed oil, myrrh oil, clove oil, niaouli oil, orange oil, *origanum* oil, Palmarosa oil, patchouli oil, Peru balsam oil, petitgrain oil, pepper oil, peppermint oil, pimento oil, pine oil, rose oil, rosemary oil, sandalwood oil, celery oil, spik oil, star anise oil, turpentine oil, *thuja* oil, thyme oil, *verbena* oil, juniper berry oil, wormwood oil, wintergreen oil, hyssop oil, cinnamon oil, citronella oil, lemon oil and cypress oil. Other fragrance and aroma compounds are ambrettolide,- amyl cinnamaldehyde, anethole, anisaldehyde, anise alcohol, anisole, methyl anthranilic acid ester, acetophenone, benzyl acetone, Benzaldehyde, ethyl benzoate, benzophenone, benzyl alcohol, benzyl acetate, benzyl benzoate, benzyl formate, benzyl valerate, borneol, bornyl acetate, α-bromostyrene, n-decylaldehyde, n-dodecyl aldehyde, eugenol, eugenol methyl ether, eucalyptol, farnesol, fenchone, fenchyl acetate, geranyl acetate, geranyl formate, heliotropin, methyl heptanecarboxylate, heptaldehyde, Hydroquinone dimethyl ether, hydroxycinnamic aldehyde, hydroxycinnamic alcohol, indole, iron, isoeugenol, isoeugenol methyl ether, isosafrole, jasmone, camphor, carvacrol, carvone, p-cresol methyl ether, coumarin, p-methoxyacetophenone, methyl-n-amylketone, methyl anthranilic acid methyl ester, p-methylacetophenone, methylchavicol, p-methylquinoline, methyl-β-naphthylketone, methyl-n-nonyl acetaldehyde, Methyl-n-nonylketone, muscone, β-naphthol ethyl ether, β-naphthol methyl ether, nerol, nitrobenzene, n-nonylaldehyde, nonylalcohol, n-octylaldehyde, p-oxy-acetophenone, pentadecanolide, β-phenylethyl alcohol, phenylacetaldehyde dimethyacetal, phenylacetic acid, pulegone, safrole, isoamyl salicylic acid ester, methyl salicylic acid ester, hexyl salicylic acid ester, cyclohexyl salicylic acid ester, santalol, skatole, terpineol, thyme, thymol, γ-undecalactone, vanillin, veratrum aldehyde, cinnamic aldehyde, cinnamic alcohol, cinnamic acid, ethyl cinnamate and benzyl cinnamate.

Other (more volatile) fragrances are alkyl isothiocyanates (alkyl legumes), butanedione, limonene, linalool, linalyl acetate and propionate, menthol, menthone, methyl-n-heptenone, phellandrene, phenylacetaldehyde, terpinyl acetate, citral and citronellal.

Preferably, mixtures of different fragrances are used, which together create an appealing scent.

Suitable perfume oils may also contain natural fragrance mixtures as available from plant or animal sources, e.g. pine, citrus, jasmine, rose, lily or ylang-ylang oil. Essential oils of lower volatility, which are mostly used as aromatic components, are also suitable as perfume oils, e.g. sage oil, chamomile oil, melissa oil, mint oil, cinnamon leaf oil, lime blossom oil, juniper berry oil, vetiver oil, olive oil, *galbanum* oil, laudanum oil, clove oil, iso-eugenol, thyme oil, bergamot oil, geranium oil and rose oil.

Compositions (T) and (M) which are exceptionally preferred according to the present disclosure are exemplified in that they contain, independently of one another, at least one fragrance in a total amount of about 0.01 to about 5 wt. %, preferably about 0.1 to about 3 wt. %, particularly preferably about 0.5 to about 2 wt. %, exceptionally preferably about 1 to about 1.5 wt. %, in each case based on the weight of the composition (T) or the composition (M).

Another object of the present disclosure is a kit for the non-oxidative dyeing of keratinous fibers, in particular human hair, with natural dyes, comprising
  a) an aqueous composition (T) having a pH in the range of from about 4.6 to about 5.6, preferably in the range of from about 4.8 to about 5.2, each measured at 20° C., wherein the composition (T) comprises:
    i. at least one polyphenol which
      is available on the Shikimate biosynthesis pathway and
      has at least 2 hydroxy groups in the molecule and
      has a molecular weight in the range from about 170 to about 20,000 g/mol; furthermore
    ii. a buffer system selected from a mixture of a moderately strong or weak acid with its conjugate or corresponding base (or the respective salt) and a mixture of a moderately strong or weak base with its conjugate or corresponding acid, and
  b) an aqueous composition (M) having a pH in the range of from about 2.5 to about 6.4, preferably in the range of from about 5.2 to about 6.0, more preferably in the range of from about 5.4 to about 5.8, in each case at 20° C., said composition (M) comprising:
    iii. at least one salt of the divalent iron cation Fe(II) in an amount of about 0.001 to about 3.0 wt. %, preferably about 0.01 to about 2 wt. %, particularly preferably about 0.1 to about 1 wt. %, exceptionally preferably about 0.2 to about 0.5 wt. %, in each case based on the weight of the composition (M),
    iv. optionally a buffer system selected from a mixture of a moderately strong or weak acid with its conjugated or corresponding base (or the respective salt) and a mixture of a moderately strong or weak base with its conjugated or corresponding acid, where none of the kit components contain elemental iron, sponge iron, copper salts or aluminum salts.

With regard to further preferred embodiments of the kits according to the present disclosure, what has been said about the methods according to the present disclosure and what has been said about the compositions (T) and (M) used according to the present disclosure applies mutatis mutandis.

Examples of Execution

The embodiments shown below are intended to explain the subject matter of the present disclosure in more detail, without limiting it herein.

Tests on the Wash Fastness of the Coloration Obtained According to the Present Disclosure in Comparison with Oxidative Hair Tinting Production of Hair Strands Dyed According to the Present Disclosure As an example of the dyeing process according to the present disclosure, the following composition (T) and the following composition (M) were prepared (all data in wt. %):

Composition (T) According to the Present Disclosure

| Matcha * | 10.00 |
|---|---|
| Xanthan gum | 1.20 |
| Trisodium citrate (anhydrous) | 1.68 |
| Citric acid (anhydrous) | 0.68 |
| Phenoxyethanol | 0.95 |
| Water, demineralized | 85.49 |
| Total | 100.00 |
| pH value (20° C.) | 5.0 |

* Japan Matcha Kakegawa, Bio/Organic; Polyphenol content: 29.1 wt. %, containing 17.1 wt. % catechins and 12 wt. % tannins; source: The Tea Company GmbH & Co. KG, DE-21629 Neu Wulmstorf Composition (M) According to the Present Disclosure

| Iron(II) lactate (anhydrous) | 1.00 |
|---|---|
| Xanthan gum | 2.00 |
| Water, demineralized | 97.00 |
| Total | 100.00 |
| pH value (20° C.) | 5.6 |

All colorizations were performed on completely unpigmented Caucasian hair type strands from Kerling International Haarfabrik GmbH (Backnang, Germany). The strands were 10 cm long, of which 8 cm were available for coloring. The remaining 2 cm at the top of the strands are used for fastening. Each strand weighed 0.45±0.05 grams.

The hair strands were treated in the composition (T) of the present disclosure (100 ml/g strand) for 30 minutes and then rinsed under running deionized water for one minute with combing 20 times.

Afterwards, the hair strands were dried with a commercial hair dryer at a defined distance (d=10 cm) and a defined temperature (T=80±5° C.) under 20-fold combing.

Immediately after completion of the drying process, the hair strands were treated for 30 minutes in the composition (M) of the present disclosure (100 ml/g strand) and then rinsed for one minute under running deionized water with combing 20 times.

Afterwards, the hair strands were dried with a commercial hair dryer at a defined distance (d=10 cm) and a defined temperature (T=80±5° C.) under 20-fold combing.

Production not According to the Present Disclosure, Oxidatively Tinted Hair Strands When selecting the oxidative hair tinting agent (see below), care was taken to ensure that the shade obtained matched as closely as possible the shade obtained by the dyeing process according to the present disclosure.

Dyeing Cream for Oxidative Hair Tinting (all Quantities in Wt. %):

| Propandiol-1.2 | 6.000 |
|---|---|
| Cetearyl alcohol | 9.000 |
| Ceteareth-20 | 2.400 |
| Steareth-100 | 0.600 |
| Paraffinum Liquidum | 2.500 |
| Glyceryl stearate | 0.500 |
| D-biotin | 0.009 |
| Sodium sulfite (anhydrous) | 1.000 |
| $Na_4$-EDTA | 0.500 |
| Bis-Diisopropanolamino-PG-Propyl Dimethicone/ Bis-Isobutyl PEG-14 Copolymer | 1.000 |
| Marine Hydrolyzed Collagen | 0.002 |
| Ascorbic acid | 0.050 |
| Ammonium sulfate | 1.000 |
| Ammonia (25 wt. %) | 0.500 |
| Perfume | 0.400 |
| p-toluenediamine sulphate | 0.125 |
| N,N-bis(2-hydroxyethyl)-para-phenylenediamine sulfate | 0.250 |
| m-Aminophenol | 0.050 |
| Resorcinol | 0.075 |
| 2,7-Dihydroxynaphthalene | 0.050 |
| Water, demineralized | 73.989 |
| Total | 100.000 |

Hydrogen Peroxide Developer for the Above Staining Cream (all Quantities in Wt. %):

| Hydrogen peroxide | 3.02 |
|---|---|
| Cetearyl alcohol | 3.60 |
| Paraffinum Liquidum | 2.00 |
| Ceteareth-20 | 1.20 |
| Propandiol-1.2 | 0.50 |
| Etidronic acid | 0.15 |
| 2,6-Dicarboxypyridine | 0.10 |
| Disodium pyrophosphate | 0.10 |
| Potassium hydroxide | 0.10 |
| Sodium benzoate | 0.04 |
| Water, demineralized | 89.19 |
| Total | 100.00 |

The dye cream listed above was mixed with the hydrogen peroxide developer listed above in a 1:1 weight ratio and applied to untreated, dry Kerling strands (as mentioned above, unpigmented, Caucasian) (9 grams of ready-to-use dye mixture per strand).

The exposure time was 20 minutes. The dye was then rinsed from the strands, and the strands were dried in a standardized manner as described above.

Determination of the Fastness to Washing of the Dyeing

Hair strands dyed according to the present disclosure and not according to the present disclosure were washed under deionized running water at a volumetric flow rate of $\dot{V}$=40±20 ml/s (T=33±2° C.) for one minute to first remove coarse impurities. Subsequently, the wet strands were hand washed up to 30 times with 0.5±0.02 g/g hair commercial shampoo (Schauma 7 herbs, Schwarzkopf pH 4.5±0.2, 12±0.5 wt. % sodium laureth sulfate (SLS)). The 7-herb shampoo was massaged 10 times with a 5-fold circular motion with thumb and index finger and constant pressure from the adhesive joint to the tip of the hair. After shampoo incorporation, hair strands were rinsed under deionized running water at a volumetric flow rate of V=40±20 ml/s (T=33±2° C.) for 1 minute. After rinsing, the hair strands were detangled by combing 20 times from the adhesive joint to the hair tip. After cleaning and combing, the hair strands were dried with a commercial hair dryer at a defined distance (d=10 cm) and temperature (T=80±5° C.). This procedure was repeated up to 30 washes of hair.

Spectrophotometric Measurement of Color Loss During Washing

In each case after 6, 12, 18, 24 and 30 shampoo washes, the hair strands were dried in an air stream and colorimetrically measured.

All colorimetric measurements were performed with the Spectraflash SF 600 colorimetric device from Datacolor.

A D65 illuminant and a diffuse/8° optical configuration were used for the spectrophotometer measurements. Spectral reflectance data for each sample from 380 nm to 700 nm were converted to colorimetric data using DCI Color software. Reflectance measurements were determined for each hair sample, with the mean of 4 measurements recorded in each case.

The color difference (ΔE) between dyed, unshampooed strand and dyed, shampooed strand was calculated according to the following formula:

$$\Delta E = \sqrt{(Lv-Ln)^2 + (av-an)^2 + (bv-bn)^2}, \text{ with}$$

Lv, av, bv: Colorimetric values before shampoo washing
Ln, an, bn: Colorimetric values after 6, 12, 18, 24 or 30 shampoo washes The smaller the color difference ΔE between dyed, unwashed strand and dyed, washed strand, the higher the wash fastness of the dyeing.

Surprisingly, it was shown that with the dyeing process according to the present disclosure, a smaller color difference ΔE between dyed, unwashed strand and dyed, washed strand could be achieved after up to 24 hair washes than with oxidative hair dyeing. Only after 30 hair washes did both dyeing methods show an almost equal degree of color loss; the value for ΔΔE was only −0.3.

Mean Value from 5 Strands in Each Case (4 Measurements Per Strand)

| Number of hair washes | Color distance ΔE present disclosure | Color distance ΔE comparison | ΔΔE |
|---|---|---|---|
| 6 | 4.4 ± 1.6 | 5.9 ± 0.4 | −1.5 |
| 12 | 7.3 ± 1.6 | 10.2 ± 0.8 | −2.9 |
| 18 | 8.4 ± 1.1 | 10.5 ± 1.1 | −2.1 |
| 24 | 9.3 ± 1.3 | 11.0 ± 0.6 | −1.7 |
| 30 | 10.9 ± 1.3 | 11.2 ± 1.0 | −0.3 |

The invention claimed is:

1. A method for the non-oxidative dyeing of keratinous fibers with natural dyes, comprising the following method steps in the order indicated:
    a) applying an aqueous composition (T) to the keratinous fibers, the aqueous composition (T) having a pH in the range from about 4.6 to about 5.6, measured at 20° C., said aqueous composition (T) comprising:
        i. a polyphenol, wherein the polyphenol;
            is available on the Shikimate biosynthesis pathway and
            has at least 2 hydroxy groups in the molecule and has a molecular weight in the range from about 170 to about 20,000 g/mol; wherein said aqueous composition (T) further comprises;
        ii. a buffer system selected from a mixture of a moderately strong or weak acid with one or more of a conjugate base of the moderately strong or weak acid, a corresponding base, or a salt of the conjugate base, and a mixture of a moderately strong or weak base with its conjugated or corresponding acid,
    b) allowing the aqueous composition (T) to act on the keratinous fibers for a time of from about 30 seconds to about 60 minutes,
    c) rinsing the keratinous fibers with water,
    d) optionally drying of the keratinous fibers,
    e) directly thereafter applying to the keratinouos fibers an aqueous composition (M) having a pH in the range from about 2.5 to about 6.4, measured at 20° C., said aqueous composition (M) comprising:
        iii. at least one salt of the divalent iron cation Fe(II) in an amount of about 0.001 to about 3.0 wt. %, based on the weight of the aqueous composition (M),
        iv. optionally a buffer system selected from a mixture of a moderately strong or weak acid with one or more of a conjugate base of the moderately strong or weak acid, a corresponding base, or a salt of the conjugate base, and a mixture of a moderately strong or weak base with its conjugated or corresponding acid,
    f) allowing the aqueous composition (M) to act on the keratinous fibers for a time of about 30 seconds to about 60 minutes,
    g) rinsing the keratinous fibers with water,
    h) optional drying of the keratin fibers,
    whereby no elemental iron, sponge iron, copper salts or aluminum salts are used in the method, and
    wherein the keratinous fibers have not been treated with an oxidizing agent and have not been treated with a keratin reducing agent for a period of at least about 7 days prior to the application of the aqueous composition (T).

2. The dyeing method according to claim 1, wherein the polyphenol is selected from tannins, pseudotannins, and mixtures thereof.

3. The dyeing method according to claim 2, wherein the tannin is selected from hydrolysable tannins, condensed tannins, and combinations thereof.

4. The dyeing method according to claim 1, wherein the polyphenol is obtained from at least one plant selected from the group of *Camellia sinensis; Acacia* spp.; i *Acacia mollissima; Acacia negra; Acacia dealbata; Olea europaea* (olive tree); *Schinopsis lorentzii; Aspidosperma quebracho-blanco; Rubiaceae Coffea arabica* L.; *Rheum* spp.; *Rheum palmatum; Pinus* spp.; *Picea* spp.; *Vitis vinifera; Lawsonia inermis* (red henna); *Quercus* spp. (oak); *Quercus macrolepis; Curcuma longa; Juglans* spp.; *Juglans nigra; Juglans regia;* tara tree; *Tara spinosa; Caesalpinia spinosa; Caesalpinia tinctoria;* chestnut (*Castanea sativa*); tanbark (*Rhus coriaria*); the wig tree; *Rhus cotinus; Cotinus coggygria; Haematoxylum brasiletto* L. (Brazilian bloodwood tree); *Haematoxylum campechianum;* bloodwood tree; bluewood tree; campeche tree; *Maclura tinctoria* (dyer's mulberry tree; and mixtures thereof.

5. The dyeing method according to claim 1, wherein the polyphenol is in the form of at least one ground plant part.

6. The dyeing method according to claim 1, wherein the polyphenol is in the form of at least one plant part extract.

7. The dyeing method according to claim 1, wherein the polyphenol is matcha.

8. The dyeing method according to claim 1, wherein the aqueous composition (T) comprises the polyphenol in an amount of from about 0.1 to about 20 weight percent, based on a total weight of the aqueous composition (T).

9. The dyeing method according to claim 1, wherien the aqueous composition (T) comprises, in each case by weight percent based on a total weight of the aqueous composition (T), matcha in an amount of from about 0.3 to about 50 wt. %.

10. The dyeing method according to claim 1, wherein the at least one salt of the divalent iron cation Fe(II) applied to the keratin fibers in step e) is selected from the group of iron(II) lactate, iron(II) gluconate, ferrous(II) citrate, ferrous (II) chloride, ferrous (II) sulfate, ferrous(II) acetate, ferrous (II) propionate, ferrous(II) oxalate, ferrous(II) malonate, ferrous(II) succinate, ferrous(II) glutarate, ferrous(II) galactose, ferrous(II) tartrate, ferrous(II) malate, and mixtures thereof.

11. The dyeing method according to claim 1, wherein the buffer system of the aqueous composition (T) comprises, based on a total weight of the aqueous composition (T), from about 0.2 to about 1.5 wt. % trisodium citrate.

12. The dyeing method according to claim 1, wherein the aqueous composition (T) is free of basic amino acids, and the aqueous composition (M) is free of basic amino acids.

13. The dyeing method according to claim 1, wherein at least one of the aqueous composition (T) or the aqueous composition (M) independently comprises at least one aliphatic solvent chosen from $C_1$-$C_4$ alkanols and $C_2$-$C_4$ polyols, in a total amount of from about 0.01 to about 8 wt. %, in each case based on a total weight of the aqueous composition (T) or a total weight of the aqueous composition (M).

14. A kit for the non-oxidative dyeing of keratinous fibers, with natural dyes, comprising
  a) an aqueous composition (T) having a pH in the range of from about 4.6 to about 5.6, measured at 20° C., wherein the aqueous composition (T) comprises:
    i. at least one polyphenol which
      is available on the Shikimate biosynthesis pathway and
      has at least 2 hydroxy groups in the molecule and
      has a molecular weight in the range from about 170 to about 20,000 g/mol; the aqueous composition (T) further comprising;
    ii. a buffer system selected from a mixture of a moderately strong or weak acid with one or more of a conjugate base of the moderately strong or weak acid, a corresponding base, or a salt of the conjugate base, and a mixture of a moderately strong or weak base with its conjugate or corresponding acid, and the kit for the non-oxidative dyeing of keratinous fibers further comprising;
  b) an aqueous composition (M) having a pH in the range of from about 2.5 to about 6.4, measured at 20° C., said aqueous composition (M) comprising:
    iii. at least one salt of the divalent iron cation Fe(II) in an amount of from about 0.001 to about 3.0 wt. %, based on a total weight of the aqueous composition (M), and
    iv. optionally a buffer system selected from a mixture of a moderately strong or weak acid with one or more of a conjugate base of the moderately strong or weak acid, a corresponding base, or a salt of the conjugate base and a mixture of a moderately strong or weak base with its conjugated or corresponding acid,
  wherein the aqueous composition (T) is free of elemental iron, sponge iron, copper salts, and aluminum salts, and the aqueous composition (M) is free of elemental iron, sponge iron, copper salts, and aluminum salts.

15. The kit according to claim 14, wherein the at least one polyphenol is selected from tannins, pseudotannins, and mixtures thereof.

16. The kit according to claim 14, wherein the aqueous composition (T) comprises the at least one polyphenol in an amount of from about 0.1 to about 20 weight percent, based on a total weight of the aqueous composition (T).

17. The kit according to claim 14, wherein the at least one salt of the divalent iron cation Fe(II) is selected from the group of iron(II) lactate, iron(II) gluconate, ferrous(II) citrate, ferrous (II) chloride, ferrous(II) sulfate, ferrous(II) acetate, ferrous(II) propionate, ferrous(II) oxalate, ferrous (II) malonate, ferrous(II) succinate, ferrous(II) glutarate, ferrous(II) galactose, ferrous(II) tartrate, ferrous(II) malate, and mixtures thereof.

18. The kit according to claim 14, wherein the aqueous composition (T) comprises the buffer system of the aqueous composition (T), and the buffer system of the aqueous composition (T) comprises, based on a total weight of the aqueous composition (T), from about 0.2 to about 1.5 wt. % trisodium citrate.

19. The kit according to claim 14, wherein the aqueous composition (T) is free of basic amino acids, and the aqueous composition (M) is free of basic amino acids.

20. The kit according to claim 14, wherein at least one of the aqueous composition (T) or the aqueous composition (M) independently comprises at least one aliphatic solvent chosen from $C_1$-$C_4$ alkanols and $C_2$-$C_4$ polyols, in a total amount of from about 0.01 to about 8 wt. %, in the case of the aqueous composition (T) based on a total weight of the aqueous composition (T), and in the case of the aqueous composition (M) based on a total weight of the aqueous composition (M).

* * * * *

UNITED STATES PATENT AND TRADEMARK OFFICE
CERTIFICATE OF CORRECTION

PATENT NO. : 12,290,584 B2
APPLICATION NO. : 18/254355
DATED : May 6, 2025
INVENTOR(S) : Lusine Sargsyan et al.

Page 1 of 1

It is certified that error appears in the above-identified patent and that said Letters Patent is hereby corrected as shown below:

In the Specification

Column 8, Line 7 change "Castatzeu sativa" to --Castanea sativa--.

Column 8, Line 35 change "Haematoxylitin brasiletto L." to --Haematoxylum brasiletto L.--.

Column 8, Line 56 change "Haematoxylum compechianum" to --Haematoxylum campechianum--.

Column 10, Line 18 change "about to about 1.5 wt.%" to --0.2 to about 1.5 wt.%--.

Column 10, Line 28 change "about to about 1.5 wt.%" to --0.2 to about 1.5 wt.%--.

Column 10, Line 38 change "about to about 1.5 wt.%" to --0.2 to about 1.5 wt.%--.

Column 10, Line 48 change "about to about 1.5 wt.%" to --0.2 to about 1.5 wt.%--.

Column 10, Line 58 change "about to about 1.5 wt.%" to --0.2 to about 1.5 wt.%--.

Column 11, Line 1 change "about to about 1.5 wt.%" to --0.2 to about 1.5 wt.%--.

Column 11, Line 11 change "about to about 1.5 wt.%" to --0.2 to about 1.5 wt.%--.

Signed and Sealed this
Fifteenth Day of July, 2025

Coke Morgan Stewart
*Acting Director of the United States Patent and Trademark Office*